(12) United States Patent
Nakanishi et al.

(10) Patent No.: US 7,345,808 B2
(45) Date of Patent: Mar. 18, 2008

(54) DEFORMABLE MIRROR AND DEVICE FOR OBSERVING RETINA OF EYE

(75) Inventors: Michiko Nakanishi, Tokyo (JP); Akio Kobayashi, Tokyo (JP); Isao Minegishi, Tokyo (JP); Ayako Iijima, Tokyo (JP)

(73) Assignee: Topcon Corporation, Tokyo (JP)

( * ) Notice: Subject to any disclaimer, the term of this patent is extended or adjusted under 35 U.S.C. 154(b) by 0 days.

(21) Appl. No.: 11/175,393

(22) Filed: Jul. 7, 2005

(65) Prior Publication Data

US 2006/0159490 A1 Jul. 20, 2006

(30) Foreign Application Priority Data

Jul. 9, 2004 (JP) .............................. 2004-203978

(51) Int. Cl.
*G02B 26/00* (2006.01)

(52) U.S. Cl. ...................................... 359/291; 359/295
(58) Field of Classification Search ................ 359/245, 359/290, 291, 295, 298, 315, 318, 846, 847; 351/221
See application file for complete search history.

(56) References Cited

U.S. PATENT DOCUMENTS 6,042,223 A 3/2000 Katakura 6,108,121 A * 8/2000 Mansell et al. ............. 359/291
6,572,230 B2 * 6/2003 Levine ....................... 351/221

FOREIGN PATENT DOCUMENTS

JP 11-137522 A 5/1999
JP 2003-125279 A 4/2003

* cited by examiner

*Primary Examiner*—Ricky Mack
*Assistant Examiner*—William Choi
(74) *Attorney, Agent, or Firm*—Foley & Lardner LLP (57) ABSTRACT

A deformable mirror, in which the distance between an electrode substrate and a membrane can be accurately maintained and which can be produced at a low material cost, is provided. The deformable mirror comprises: an electrode substrate 11 having a plurality of electrodes (16a, 16b, 16c, 16d and 16e) formed on a surface of the electrode substrate; a silicon membrane 13 having a counter electrode opposed to the plurality of electrodes formed on the electrode substrate 11; a reflection section 15 provided on the side of the silicon membrane 13 opposite the counter electrode; and a support plate 19 integrally bonded to the electrode substrate 11 for restraining the displacements of the plurality of electrodes which adversely affect the deformation of the silicon membrane 13, in which a plurality of layers of wiring patterns (11a, 11b, 11c, 11d and 11e) for supplying drive voltages to the plurality of electrodes are formed in the electrode substrate 11.

14 Claims, 7 Drawing Sheets

Before bonding

Horizontal axis: position on substrate (mm)

FIG. 5B

After bonding

Horizontal axis: position on substrate (mm)

FIG. 6

DEFORMABLE MIRROR AND DEVICE FOR OBSERVING RETINA OF EYE

BACKGROUND OF THE INVENTION

1. Technical Field

The present invention relates to a deformable mirror appropriate for use in retinal cameras, heads-up displays, astronomical telescopes, laser irradiation devices and so on. The present invention is also relates to a device for observing the retina of an eye that casts light beam from a photographing light source to an eye to be examined and records the image of the light beam reflected from the retina of the eye as a retinal image, for diagnosing the retina of the eye.

2. Related Art

However, since a human eye optical system is not ideal as a photographing object, sufficient resolution cannot be necessarily achieved. Therefore, in order to compensate for the deformation of the wavefront of a human eye optical system, deformable mirrors using a piezoelectric effect have been in use.

The device such as a camera for observing the retina of an eye is used by ophthalmologists and ophthalmic opticians to photograph the image of the retina of an eye for inspecting the state of the retina, hemorrhage on the retina of the eye, and so on. Incidentally, the human eyes optical system is composed of the cornea, the lens, the vitreous body and others with, unlike an ideal optical system used as a basis of the geometrical optics, some deformation. In particular in the clinical field of ophthalmology, the image of the retina of the eye is required to be clear and of little aberration because the extent of difference of the examined eye from a normal eye is used as diagnosis information. However, because the optical system for the human eyes constituting the photographing device is not ideal, in some cases sufficient resolution cannot be achieved. Therefore, to compensate for the deformation of the wavefront of the optical system for the human eyes, the deformable mirrors using the piezoelectric effect have been in use.

However, the conventional deformable mirrors using the piezoelectric element require a high voltage applied to the piezoelectric element and needs to use, as an electronic control circuit, a piezoelectric element with a high dielectric strength that is expensive. Therefore, commercially available retinal cameras employ deformable mirrors using electrostatic attraction that can be actuated with a lower drive voltage in comparison with the piezoelectric type.

In the case of a deformable mirror using electrostatic attraction, however, electrodes are arranged at a high density so that the deformation of the mirror can be controlled minutely. To prevent a creeping discharge and a dielectric breakdown between the electrodes and the wires, there should be proper intervals between them. For example, to prevent a creeping discharge, there should be intervals of at least 0.2 to 0.3 mm for a drive voltage of 300V.

Conventionally, a single-piece glass or ceramics substrate is used as an electrode substrate for a deformable mirror. In the conventional structure, the wiring of the electrode substrate is made by directing the wires from the front side to the back side of the electrode substrate by through-hole processing and connecting the wires to a connector cable through the two layers on the front and back sides. However, when a drive voltage of a few hundred volts is used, the degree of freedom in the layout of the wiring is too low with a two-layer structure to satisfy the necessity of providing sufficient intervals suitable for a high voltage between the wires and arranging the electrodes at a high density. On the other hand, when a ceramics substrate on which wiring can be formed in multiple layers is used as the electrode substrate, there are advantages that a desired flatness can be achieved by processing and that a material with an expansion coefficient close to that of the membrane can be selected, but there is also a disadvantage that the material and processing costs are high.

The present invention has been made to solve the above problems and it is, therefore, an object of the present invention to provide a deformable mirror in which the distance between an electrode substrate and a membrane can be accurately maintained and which can be produced at a low material cost.

SUMMARY OF THE INVENTION

Figure 1A:
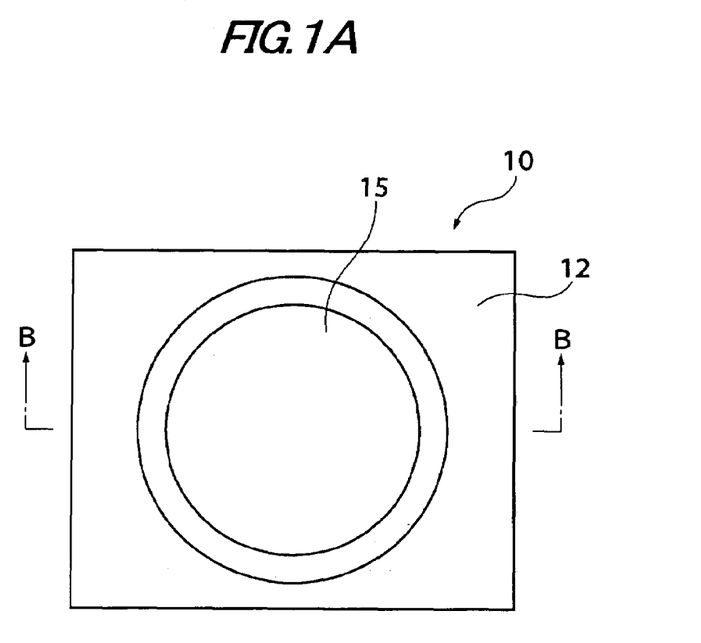
FIG. 1A is a plan view illustrating the constitution of one embodiment of the present invention.
Figure 1B:
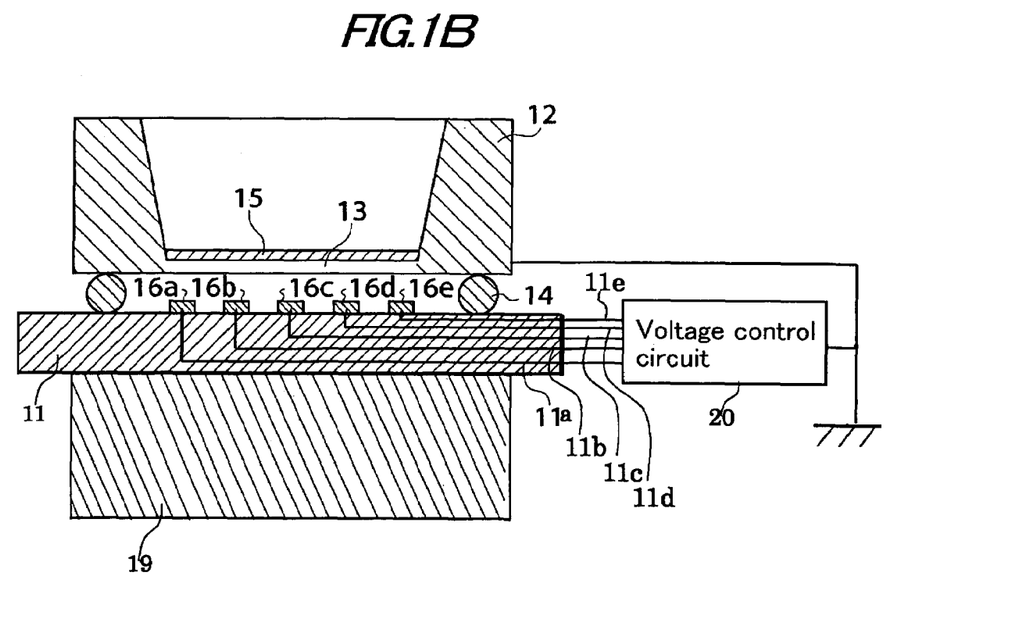
FIG. 1B is a cross-sectional view taken on the plane of the line B—B of FIG. 1A.

A deformable mirror of the present invention accomplishing the above object comprises, as shown in FIG. 1B for example, an electrode substrate 11 having a plurality of electrodes (16a, 16b, 16c, 16d and 16e) formed on a surface of the electrode substrate 11; a silicon membrane 13 having a counter electrode opposed to the plurality of electrodes formed on the electrode substrate 11; a reflection section 15 provided on a side of the silicon membrane 13 opposite the counter electrode; and a support plate 19 integrally bonded to the electrode substrate 11 for restraining displacements of the plurality of electrodes which adversely affect deformation of the silicon membrane 13, wherein a plurality of layers of wiring patterns (11a, 11b, 11c, 11d and 11e) for supplying drive voltages to the plurality of electrodes are formed in the electrode substrate 11.

In a device constituted as described above, since the support plate 19 with high rigidity is bonded to the electrode substrate 11, the deformation, such as warp, of the electrode substrate 11 can be small in comparison with when only the electrode substrate 11 is used and the displacements of a plurality of the electrodes can be suppressed. Also, since wiring pattern layers for supplying drive voltages to the electrodes are formed in plural layers on the electrode substrate 11, it is possible to provide sufficient intervals suitable for a high voltage between the wires and to arrange the electrodes at a high density. Therefore, when drive voltages are applied to the electrodes to control the deformation of the silicon membrane 13, the deformation of the silicon membrane 13 is not affected by the warp or the like of the electrode substrate 11.

It is preferable in the deformable mirror of the present invention that the support plate 19 has sufficient rigidity to suppress the displacements of the plurality of electrodes formed on the electrode substrate 11 caused by deformation stress of the electrode substrate 11 to one-tenth or less of a distance between the electrodes. Then, even if the temperature in the environment in which the device is used varies, the electrode substrate 11 is not deformed to the extent that its performance would be impaired since the support plate 19 has sufficient rigidity to suppress the thermal deformation of the electrode substrate 11. Therefore, the displacements of the electrodes 16 formed on a surface of the electrode substrate 11 are prevented.

Figure 2A:
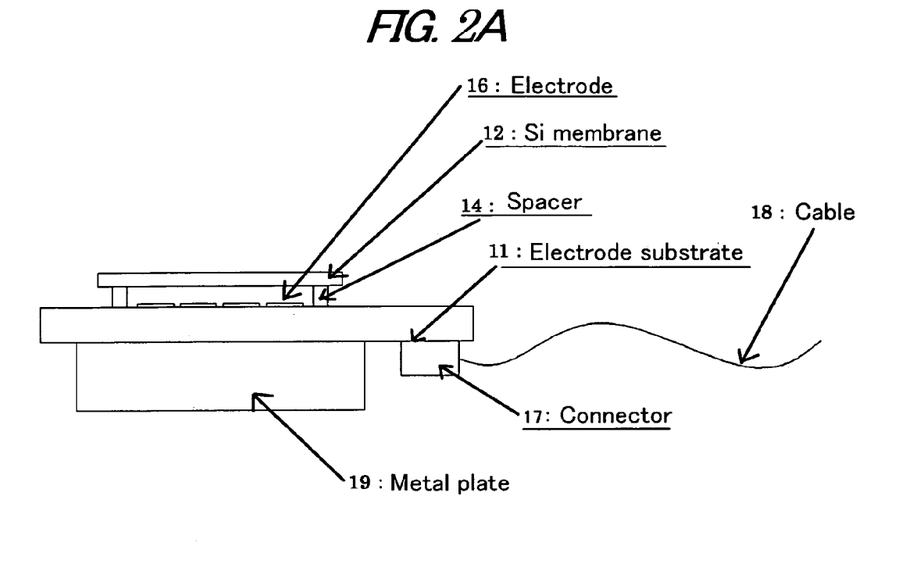
FIG. 2A is a cross-sectional view illustrating the constitution of the device shown in FIG. 1A.
Figure 2B:
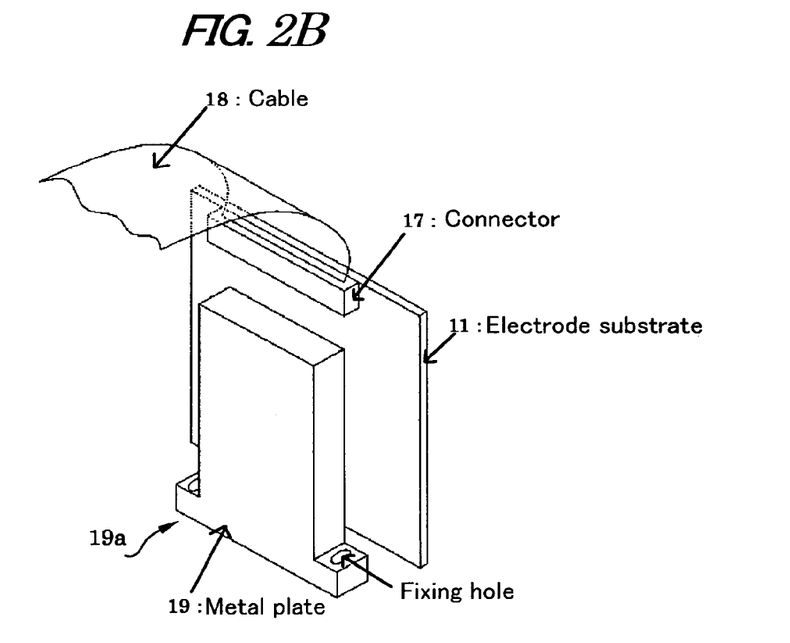
FIG. 2B is a perspective view illustrating the constitution of the device shown in FIG. 1A.

It is preferable in the deformable mirror of the present invention that, as shown in FIG. 2B for example, the support plate 19 has a reference surface for attachment. With the above constitution, since the deformable mirror can be attached to a device such as a device for observing the retina of an eye with reference to the support plate 19, the work of incorporating the deformable mirror into the device for observing the retina of an eye can be conducted smoothly and there is no need for complicated adjusting operation.

It is preferable in the deformable mirror of the present invention that, as shown in FIGS. 2A and 2B for example, a cable 18 is connectable to the electrode substrate 11 via a connector 17, and the support plate 19 has sufficient rigidity to suppress deformation of the electrode substrate 11 caused by deformation stress of the electrode substrate. With the above constitution, since the stress caused by installation of the deformable mirror and wiring of the cable 18 during incorporation of the deformable mirror into the device for observing the retina of an eye does not adversely affect the silicon membrane 13 and the electrodes 16, stable performance can be achieved.

It is preferable in the deformable mirror of the present invention that materials having generally the same thermal expansion coefficients are selected as materials for the support plate 19 and the electrode substrate 11. With the above constitution, even if the temperature in the environment in which the device is used varies, it does not cause performance degradation of the deformable mirror since the thermal expansion coefficients of the support plate 19 and the electrode substrate 11 are generally the same.

It is preferable in the deformable mirror of the present invention that the electrode substrate 11 is made of a glass-epoxy resin material and the support plate 19 is made of a stainless steel plate material.

Figure 3A:
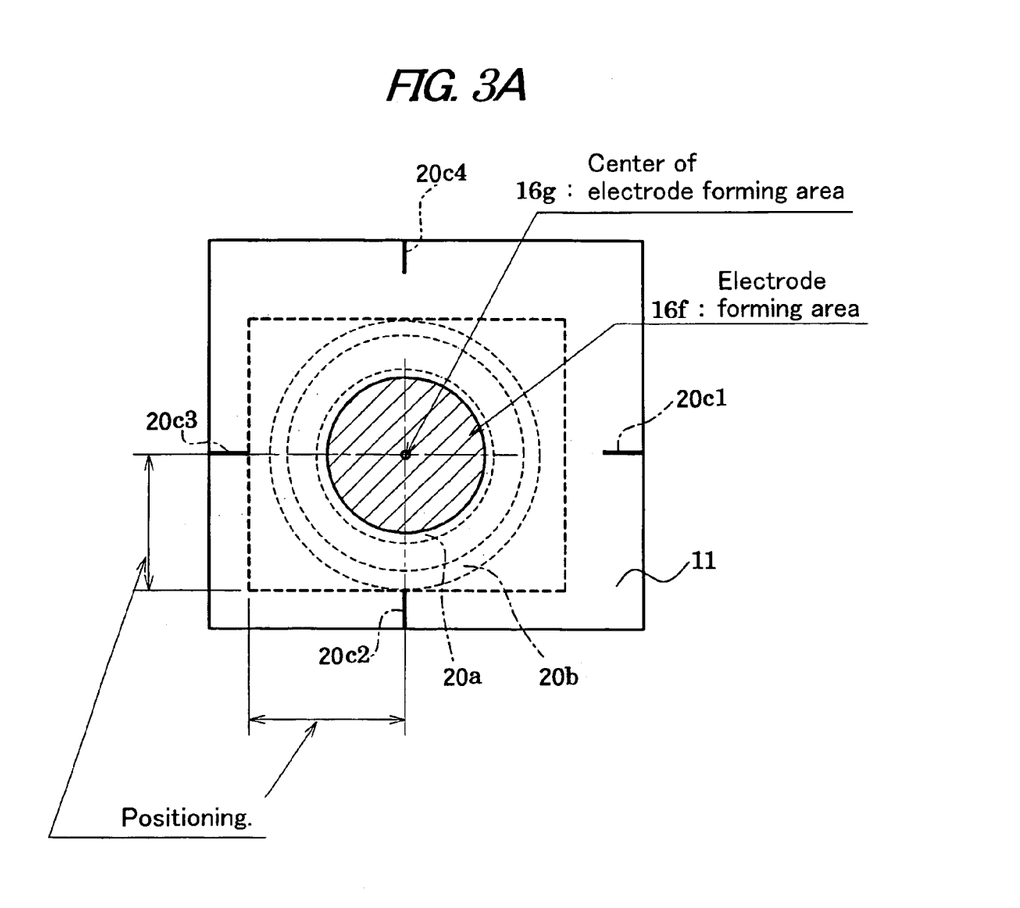
FIG. 3A is a plan view for explaining the positioning of an electrode substrate and a metal plate.

A deformable mirror of the present invention accomplishing the above object comprises, as shown in FIG. 1B for example, an electrode substrate 11 having a plurality of electrodes (16a, 16b, 16c, 16d and 16e) formed on a surface of the electrode substrate 11; a silicon membrane 13 having a counter electrode opposed to the plurality of electrodes formed on the electrode substrate 11; a reflection section 15 provided on a side of the silicon membrane 13 opposite the counter electrode; a spacer 14 for maintaining a distance between the silicon membrane 13 and the electrode substrate 11 at a specific value; and a support plate 19 integrally bonded to the electrode substrate 11 for restraining displacements of the plurality of electrodes which adversely affect deformation of the silicon membrane 13. And as shown in FIG. 3A for example, an area of the electrode substrate 11 to which the support plate 19 is integrally bonded includes a counter electrode opposing area 20a opposed to an area of the silicon membrane 13 having the counter electrode, a spacer attaching area 20b to which the spacer 14 is attached, and an electrode forming area 16f in which the plurality of electrodes of the electrode substrate 11 are formed.

Figure 7:
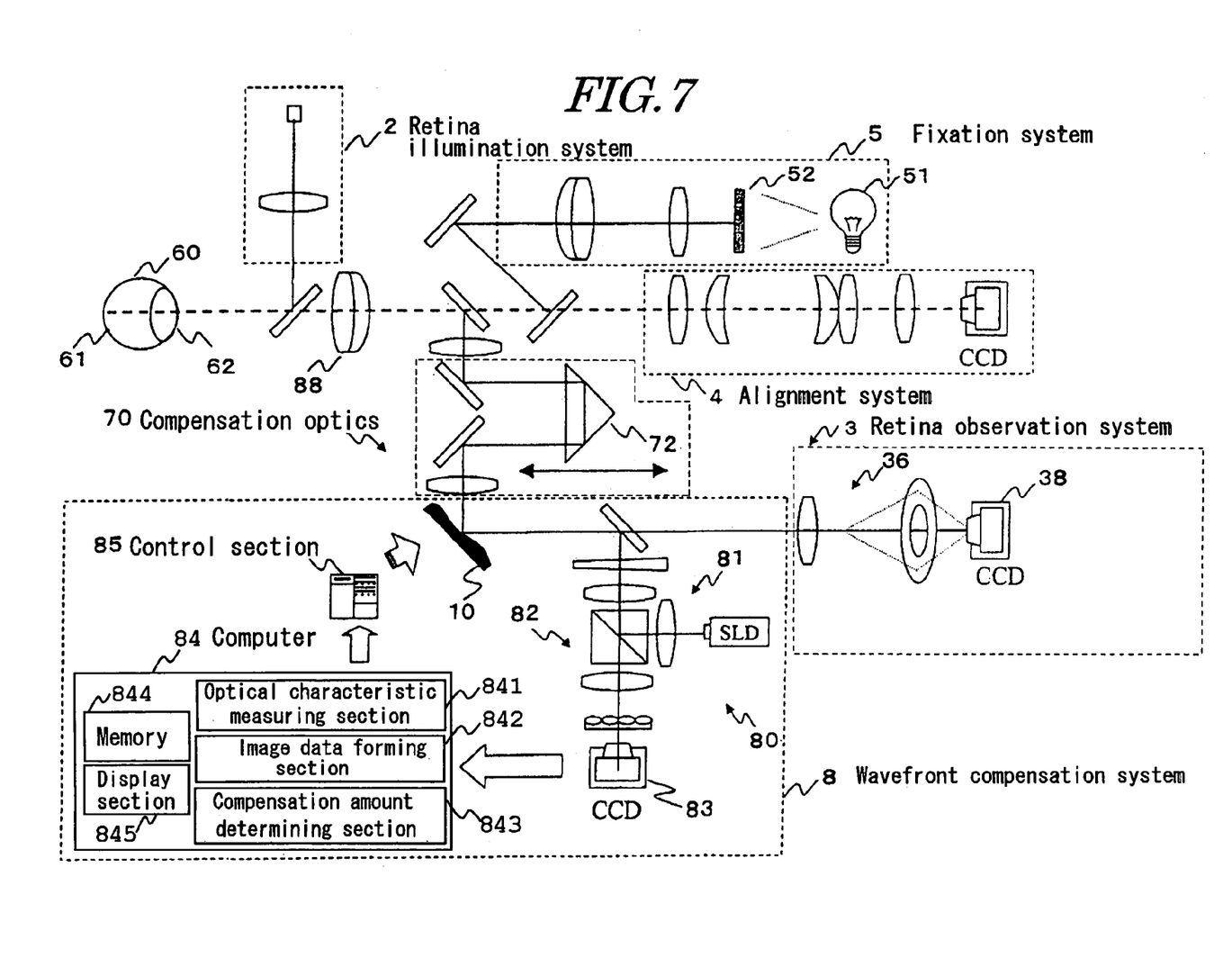
FIG. 7 is a constitutional block diagram illustrating the entire device for observing the retina of an eye.

A device for observing a retina of an eye of the present invention is, as shown in FIG. 7 for example, configured to use the deformable mirror according to any of claim 1 to claim 7.

In the deformable mirror according to the present invention constituted as described above, a multilayer printed board can be used as the electrode substrate 11, which contributes to the reduction of the production costs. Also, when a surface of the electrode substrate 11 is smoothed to a flatness of approximately a few μm in accordance with a surface of the support plate 19, a plurality of electrodes can be formed on the surface of the electrode substrate 11 to allow it to be used in a deformable mirror. It is, therefore, possible to effectively cope with a trend toward a high drive voltage and multiple electrodes.

In the device for observing the retina of an eye according to the present invention, the distances between the membrane 13 and the electrodes 16 of the deformable mirror of the present invention can be large so that the deformable mirror 10 can be actuated with a high drive voltage. Therefore, a large amount of aberration which can continuously cover the intervals of the refractive powers of cylindrical lenses for use in a device for observing the retina of an eye can be compensated.

The basic Japanese Patent Application No. 2004-203978 filed on Jul. 9, 2004 is hereby incorporated in its entirety by reference into the present application.

The present invention will become more fully understood from the detailed description given hereinbelow. The other applicable fields will become apparent with reference to the detailed description given hereinbelow. However, the detailed description and the specific embodiment are illustrated of desired embodiments of the present invention and are described only for the purpose of explanation. Various changes and modifications will be apparent to those ordinary skilled in the art within the spirit and scope of the present invention on the basis of the detailed description.

The applicant has no intention to give to public any disclosed embodiments. Among the disclosed changes and modifications, those which may not literally fall within the scope of the present claims constitute, therefore, a part of the present invention in the sense of doctrine of equivalents.

The use of the terms "a" and "an" and "the" and similar referents in the context of describing the invention (especially in the context of the following claims) are to be construed to cover both the singular and the plural, unless otherwise indicated herein or clearly contradicted by context. The use of any and all examples, or exemplary language (e.g., "such as") provided herein, is intended merely to better illuminate the invention and does not pose a limitation on the scope of the invention unless otherwise claimed.

DETAILED DESCRIPTION OF THE PREFERRED EMBODIMENT

Description will be hereinafter made of the embodiments of the present invention in detail with reference to the drawings.

First Embodiment

FIG. 1 is a construction diagram illustrating one embodiment of the present invention, in which FIG. 1A is a plan view and FIG. 1B is a cross-sectional view taken on the plane of the line B—B of FIG. 1A and includes a voltage control circuit. As shown in the drawing, a deformable mirror according to the present invention comprises a printed board 11 as an electrode substrate; a membrane 13 as a silicon membrane; spacers 14; a reflection coating 15; electrodes 16; a metal plate 19 as a support plate; and a voltage control circuit 20.

The electrode substrate 11 is, for example, a low-expansion, multilayer printed board made of a glass-epoxy resin, having a thermal expansion coefficient α of 8 to 12 [ppm/° C.]. The multilayer printed board for use as the electrode substrate 11 has warp as a whole since it is made by press-molding and cut after surface polishing. Thus, to minimize the warp, it is preferably made of a multilayer printed board material which has resistance to warp. Wiring patterns 11a, 11b, 11c, 11d and 11e for supplying drive voltages to electrodes 16a, 16b, 16c, 16d and 16e, respectively, are formed in the plural layers of the multilayer printed board.

A silicon substrate 12 is a mono- or multi-crystalline silicon substrate and has a thickness of approximately 0.5 mm. The membrane 13 is formed by selective etching of the silicon substrate 12 and has flexibility and a thickness of approximately 4 μm, for example.

The spacers 14 are used to maintain the gap between the membrane 13 and the electrodes 16 at a specific value and are balls with high rigidity, for example. A prescribed number of electrodes 16 are formed on the printed board 11. The reflection coating 15, which is formed by deposition of a material with high reflectivity on the membrane 13, is a film of a metal with a high reflectivity such as aluminum. The electrodes 16a, 16b, 16c, 16d and 16e are actuated individually by the voltage control circuit 20.

The metal plate 19 has a surface finished to a desired flatness of a few μm, for example, and made of a material with a thermal expansion coefficient 9.8 to 10.4 [ppm/° C.] which is generally equal to the thermal expansion coefficient α of the electrode substrate 11 such as 18% Cr stainless steel (JIS SUS430) or 18% Cr-8% Ni stainless steel (JIS SUS304). The metal plate 19 is bonded on the surface of the electrode substrate 11 opposite the surface on which the electrodes are formed. Since the thermal expansion coefficients of the metal plate 19 and the electrode substrate 11 are close to each other, the influence of deformation caused by a change in environmental temperature is suppressed. When the metal plate 19 is directly attached to a device for observing the retina of an eye, the surface bonded to the electrode substrate 11 should be perpendicular to the surface attached to the device. For example, the tilt angle of the surface with respect to the surface attached to the device is preferably within a few arc-minutes, although it depends on the drawing distance of the light beam from the retinal camera.

FIG. 2 is a construction diagram of the device shown in FIG. 1, in which FIG. 2A is a cross-sectional view and FIG. 2B is a perspective view. In FIGS. 2A and 2B, a connector 17 and a cable 18 are additionally shown while the wiring patterns 11a, 11b, 11c, 11d and 11e and the voltage control circuit 20 are not shown. The connector 17 and the cable 18 are conductors for directing the drive voltages sent from the voltage control circuit 20 to the electrodes 16 and are attached to the multilayer printed board as the electrode substrate 11. Stress is applied to the electrode substrate 11 depending on how the cable 18 is wired, and the electrode substrate 11 is deformed. However, since the metal plate 19 has high rigidity, the deformation of the electrode substrate 11 does not cause deformation of the bonded part of the metal plate 19. Thus, the characteristics of the deformable mirror are not changed due to the wiring of the cable 18.

When the metal plate 19 is provided with fixing holes or taps for fixing it to the device, the metal plate 19 can be directly attached to the device. A reference surface 19a is provided on the bottom of the metal plate 19 and can be used for positioning of the electrode substrate 11 when it is bonded. When the reference surface 19a of the metal plate 19 is positioned on the installation reference surface of the device for observing the retina of an eye, the position of the deformable mirror with respect to the device for observing the retina of an eye can be easily determined. Also, when the membrane 13 is placed over the electrode substrate 11, the membrane 13 can be placed in a desired position by placing it with reference to the reference surface 19a of the metal plate 19.

Figure 3B:
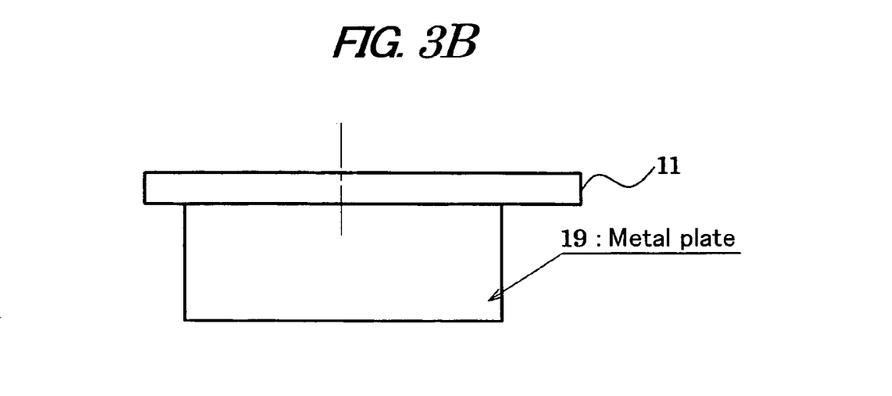
FIG. 3B is a side view for explaining the positioning of the electrode substrate and the metal plate.

The assembly of the device with the above constitution is described. FIG. 3 is a view for explaining the positioning of the electrode substrate and the metal plate, in which FIG. 3A is a plan view and FIG. 3b is a side view. Since the accuracy of the external dimensions and the surface pattern of the electrode substrate 11 is typically as low as approximately ±0.3 mm, position control based on the external dimensions of the electrode substrate 11 is difficult to perform. It is, therefore, preferred to perform position control with reference to the electrode pattern on the surface of the electrode substrate 11. For example, reference line patterns 20c1 to 20c4 with a length of 0.1 mm whose extensions pass through the center of the electrode pattern on the surface of the electrode substrate 11 are provided at the four sides of the surface of the electrode substrate 11. The reference line patterns 20c1 to 20c4 and the reference surface of the metal plate 19 are positioned, using an assembling tool (not shown), at a positioning accuracy higher than the width of the line patterns under a microscope. Then, the center 16g of an electrode forming area on the electrode substrate 11 and an attachment reference surface of the metal plate 19 are properly positioned and the electrode substrate 11 and the metal plate 19 are bonded together.

It is preferred to select an adhesive with a thermal expansion coefficient which is close to those of the metal plate 19 and the electrode substrate 11. When such an adhesive is not available, it is preferred to use an adhesive which forms as thin an adhesive layer as possible. Also, the use of an adhesive which has sufficient bonding strength in the environmental temperature range in which the device is used is preferred.

The wiring in each layer of the multilayer printed board should be formed properly within an electrode forming area 16f in which the electrodes 16 are formed in order to improve the flatness of the electrode forming area 16f of the electrode substrate 11. For example, it is preferred to form such wiring patterns that the overlap between the copper lines as wiring material for the multilayer printed board and prepreg bonded to fill the gaps between the copper lines can be uniform in the electrode forming area 16f.

The area of the electrode substrate 11 to which the support plate 19 is integrally bonded preferably includes a counter electrode opposing area 20a opposed to the area of the silicon membrane 13 having a counter electrode, a spacer attaching area 20b to which the spacers 14 are attached, and the electrode forming area 16f, in which the electrodes of the electrode substrate 11 are formed.

Figure 4:
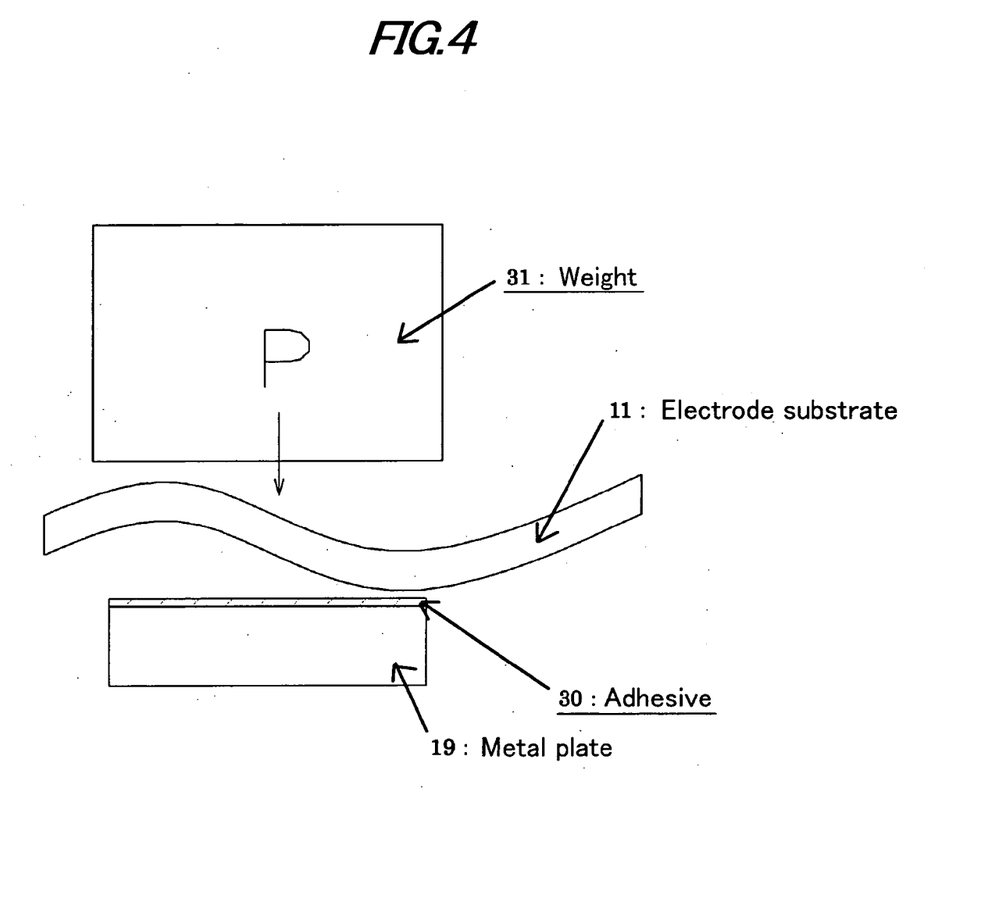
FIG. 4 is an explanatory view of the bonding of the electrode substrate and the metal plate.

FIG. 4 is an explanatory view of the bonding of the electrode substrate and the metal plate. First, an adhesive is applied on the metal plate 19 and the electrode substrate 11 is placed on the metal plate 19. Then, a weight is put on the electrode substrate 11 so that the electrode substrate 11 can change its shape in conformity with the shape of the surface of the metal plate 19. The part of the weight 31 to be in contact with the electrode substrate 11 is preferably finished to a flatness of a few μm or less. The weight of the weight 31 is approximately 10 kg for an area of 20×20 mm, for example. The adhesive 30 preferably has a thermal expansion coefficient close to those of the metal plate 19 and the electrode substrate 11 and can have sufficient bonding strength in the environmental temperature range in which the device is used.

The electrode substrate 11 may be shaped by clamping it with plates with controlled flatness, applying weight to it, and heating it to a temperature higher than its glass transition point so that it can have a desired flatness and then be bonded to the metal plate 19. The area where the metal plate 19 as a support plate is in contact with the electrode substrate 11, preferably includes the silicon membrane 13 having a counter electrode, the spacers 14 for connecting the electrode substrate 11 and the electrode forming area.

Next, a comparative example is described, in which a multilayer printed board which is not reinforced by a metal plate is used as the electrode substrate 11. In general, the flatness of a multilayer printed board including warp is approximately the same as the thickness of the multilayer printed board. The printed board 11 has residual stress introduced during the production process and may be deformed due to the change of the temperature in the environment in which it is used. When the printed board 11 is deformed, the distances between the electrodes and the membrane 13 is changed resulting in the change of the characteristics of the deformable mirror.

In the deformable mirror, the distances between the electrodes 16 and the membrane 13 are in the order of a few dozen μm. The maximum amount of deformation of the membrane 13 is determined according to the distances between the electrodes 16 and the membrane 13. When the membrane 13 is deformed to the extent that exceeds one third of the distances between the electrodes 16 and the membrane 13, the membrane 13 may be pulled in and adhere to the electrodes 16. Also, when the distances between the electrodes 16 and the membrane 13 varies, the electric field applied to the membrane 13 (the voltage (V)/the distances between the electrodes 16 and the membrane 13 (mm)) is varied even if the same voltage is applied and accurate control cannot be achieved. Moreover, since the flatness of the printed board 11 is not high, the deformable mirror cannot exhibit satisfactory performance when the distances between the electrodes 16 and the membrane 13 is not uniform.

In another example, the membrane 13 is placed above a surface of the electrode substrate 11 with a spacer 14 interposed to provide a distance therebetween in order to reduce the influence of warp of the multilayer printed board. In this case, however, the deformation of the electrode substrate 11 influences the membrane 13 and stress is applied to the membrane 13. Then, even if the voltage control circuit 20 supplies control voltages to the electrodes 16, the membrane 13 cannot be deformed to a desired shape and the shape of the reflection coating 15 cannot be controlled appropriately.

Figure 5A:
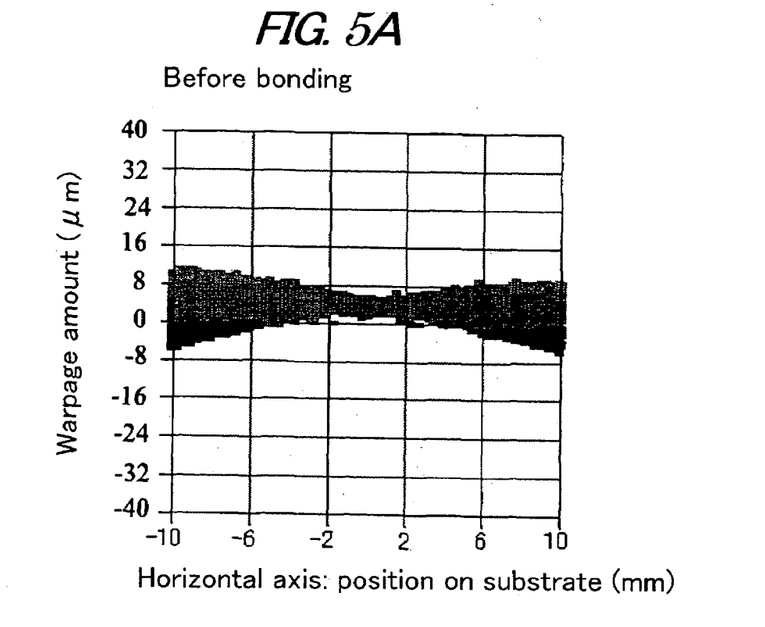
FIG. 5A is an explanatory diagram of the warp of the electrode substrate before bonding the metal plate thereto.
Figure 5B:
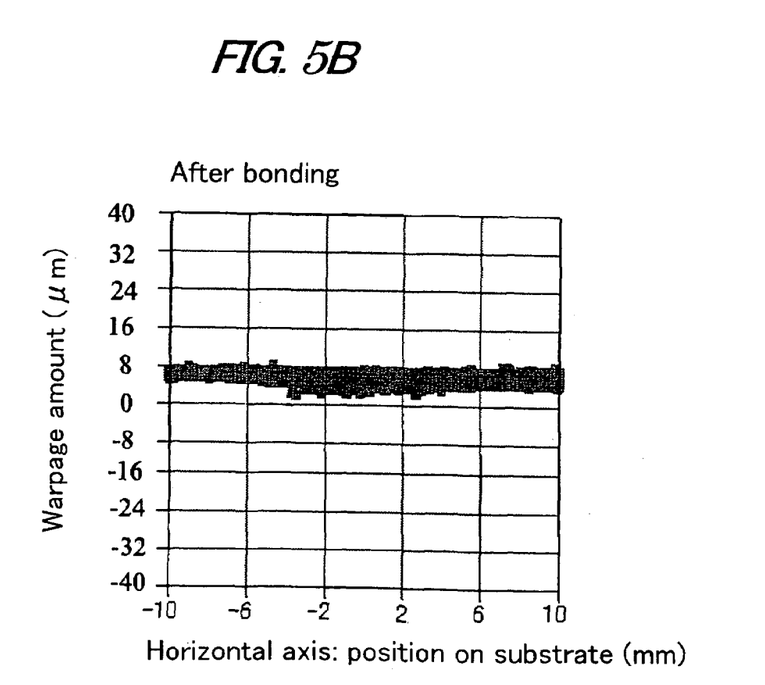
FIG. 5B is an explanatory diagram of the warp of the electrode substrate after bonding the metal plate thereto.

FIG. 5 shows explanatory diagrams of the warp of the electrode substrate before and after the bonding of the metal plate, in which FIG. 5A shows the warp before the bonding and FIG. 5B shows the warp after the bonding. In the diagrams, the horizontal axis represents the position on the substrate (mm), and the vertical axis represents the amount of warp (μm), and the distribution of the amounts of warp of the electrode substrate 11 is shown with reference to a warp amount of 0 μm. The initial warp amount of the electrode substrate 11 is approximately 20 μm, whereas the warp amount after the bonding of the metal plate 19 is reduced to approximately 5 μm. The electrode substrate 11 can be satisfactorily used as the electrode substrate 11 for a deformable mirror.

Figure 6:
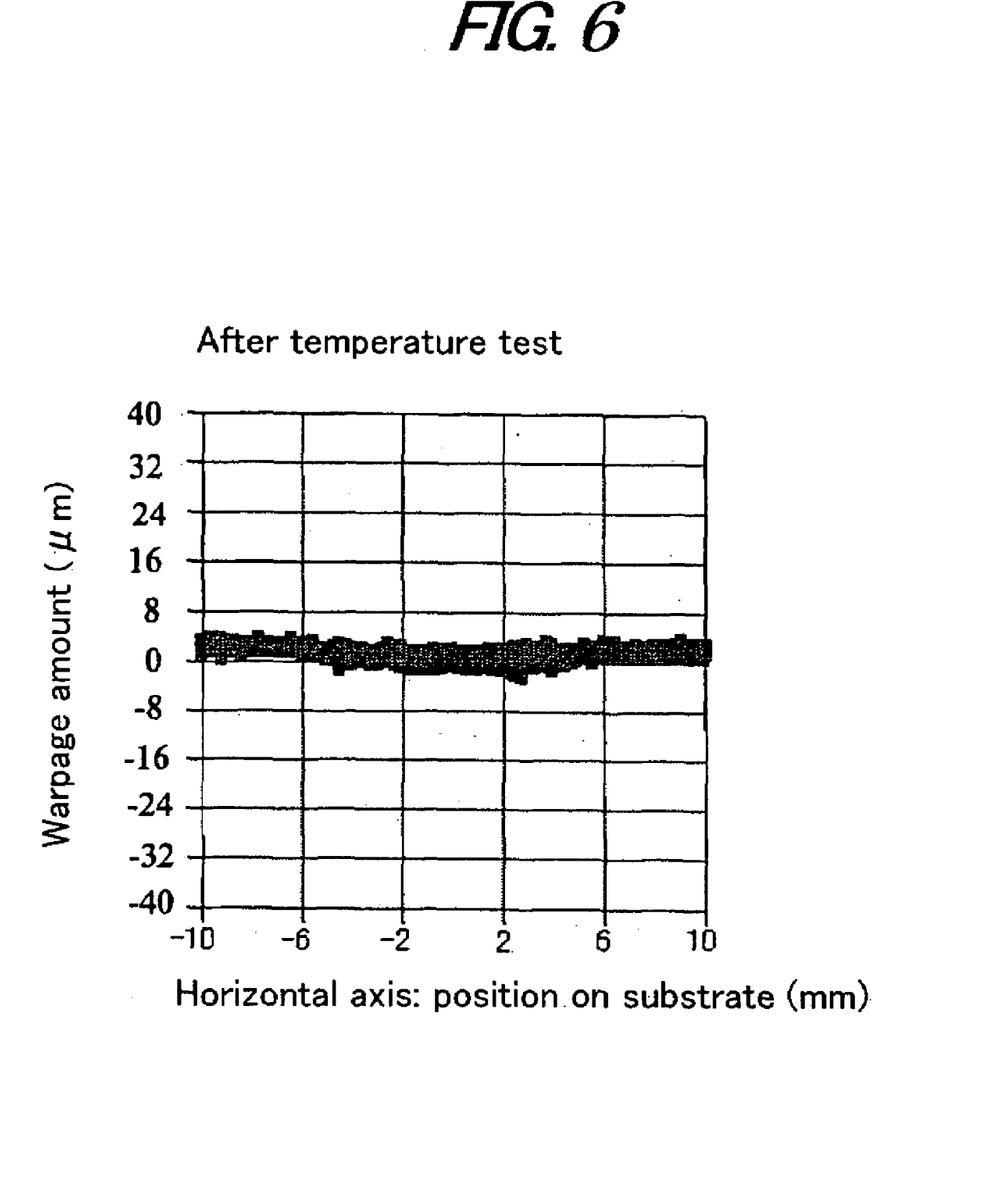
FIG. 6 is an explanatory diagram of the warp of the electrode substrate after an environmental temperature test.

FIG. 6 is an explanatory diagram of the warp of the electrode substrate after an environmental temperature test. The present inventors placed the electrode substrate 11 after the bonding in a constant-temperature oven and checked whether its surface shape was changed or not on an environmental temperature test. As can be seen from the comparison between FIG. 6 and FIG. 5B, the surface shape was not changed but stable before and after the test. That is, stress is hardly generated between the electrode substrate 11 and the metal plate 19 by the change of the environmental temperature because the thermal expansion coefficients of the electrode substrate 11 and the metal plate 19 are close to each other. This is believed to be because the electrode substrate 11 with the metal plate 19 bonded thereto is stable against changes of the environmental temperature.

Second Embodiment

Next, a device for observing the retina of an eye employing the above deformable mirror 10 is described. FIG. 7 is a constitutional block diagram illustrating the entire device for observing the retina of an eye. As shown in FIG. 7, the device for observing the retina of an eye includes: a wavefront compensation system 8, a retina illumination system 2, a retina observation system 3, an alignment system 4, a fixation system 5, and a compensation optics 70. The wavefront compensation system 8 has: a wavefront measuring system 80 including a point image projection optical system 81, a point image reception optical system 82, and a point image receiving section 83 (CCD); a computer 84; and a control section 85. The computer 84 includes: an optical characteristic measuring section 841, an image data forming section 842, a compensation amount determining section 843, a memory 844, and a display section 845.

The retina illumination system 2 includes: a second light source section, a condenser lens, and a beam splitter, to cast the second light beam of the second light source section to a specified area on the retina of an examined eye. The retina observation system 3 includes a retinal image forming optical system 36 and a retinal image receiving section 38 (CCD). The retinal image forming optical system 36 includes for example an afocal lens 88, a compensation optics 70, a condenser lens, and a beam splitter, to guide the light reflected from the retina 61 through the compensation optics 70 to the retinal image receiving section 38. The compensation optics 70 has: the deformable mirror 10 for compensating aberration of measurement light, and a movable prism and a spherical lens that move in the optical axis direction to compensate spherical components of the aberration. The compensation optics 70 is placed in the point image projection optical system 81 and the retinal image forming optical system 36 to compensate aberration of the light beam reflected back for example from the examined eye 60.

The alignment system 4 includes a condenser lens and an alignment light receiving section to guide the light beam emitted from the light source section and coming back as reflected from the cornea 62 of the examined eye 60 to the alignment light receiving section. The fixation system 5 includes a light path for casting a target for fixation and fogging of the examined eye 60 for example, and has a third light source section 51, a fixation target 52, and a relay lens. It is possible to cast the fixation target 52 with the light beam from the third light source 51 to the retina 61 so that the examined eye 60 observes the image.

The optical characteristic measuring section 841 determines optical characteristics including aberration of higher orders of the examined eye 60 according to the output from the point image receiving section 83. The image data forming section 842 carries out simulation of perceived state of the target according to the optical characteristics, and calculates data of the examined eye such as MTF indicating the perceived state or simulation image data. The memory 844 stores a plurality of voltage change templates for adjusting the deformable mirror 10. The compensation amount determining section 843 chooses from the voltage change templates stored in the memory 844 and, according to the voltage change template chosen, determines a compensation amount for the deformable mirror 10, and outputs the compensation amount to the control section 85. The control section 85 deforms the deformable mirror 10 according to the output from the compensation amount determining section 843. Further details of the device for observing the retina of an eye are described for example in the specification of a Japanese patent application No. 2003-125279 relating to the proposal of the applicant of the present invention.

As has been described above, according to the embodiment of the deformable mirror of the present invention, since a surface of the printed board 11 is smoothed to a flatness of approximately a few μm in accordance with a surface of the metal plate, the printed board 11 can be used as the electrode board 11 of a deformable mirror. Thus, a multilayer printed board which is relatively inexpensive can be used as the electrode substrate 11. Also, since a multilayer printed board can be used as the electrode substrate 11, higher drive voltages can be applied to the electrodes and the number of the electrodes can be increased to control the shape of the membrane minutely. In addition, the opening in an upper area of the silicon substrate 12 can be closed with a glass plate. Then, the silicon membrane 13 can be protected from damage during handling and adhesion of dust to the silicon membrane 13 can be prevented.

When the deformable mirror according to the present invention is applied to a device for observing the retina of an eye, the following effects can be achieved. The reflected light from the retina of an examined eye 60 includes aberration since the human eye optical system is not ideal and a clear image of the retina is not obtained. Thus, in current retinal cameras, the cylinder component (Zernike (2.±2) component) is compensated by placing a compensation cylindrical lens in a light path. However, the intervals between the refractive powers of cylindrical lenses are limited to certain values (for example, intervals of 3 D (diopters)) and it is impossible to obtain a clear and fully aberration-compensated image of the retina. This type of optical distortion can be compensated by the deformable mirror 10. When the distance between the membrane and the electrodes is increased and the deformable mirror 10 is actuated with a high voltage, large aberration which can continuously cover the intervals between the refractive powers of cylindrical lenses can be compensated. Also, when the number of the electrodes below the membrane is increased, complicated aberration can be compensated.

Here is the list of the primary reference numerals used in the above description. 10: deformable mirror, 11: electrode substrate (printed board), 20*a*: counter electrode opposing area, 20*b*: spacer attaching area, 13: membrane (silicon membrane), 14: spacer, 15: reflection section, 16: electrode, 16*f*: electrode forming area, 17: connector, 18: cable, and 19: metal plate (support plate).

What is claimed is:

1. A deformable mirror comprising:
    an electrode substrate having a plurality of electrodes formed on a surface of the electrode substrate;
    a silicon membrane configured as a counter electrode, and having an electrode side opposed to the plurality of electrodes formed on the electrode substrate;
    a reflection section provided on a side of the silicon membrane opposite the electrode side; and
    a support plate integrally bonded to the electrode substrate for restraining deformation of the electrode substrate,
    wherein a plurality of layers of wiring patterns for supplying drive voltages to the plurality of electrodes are formed in the electrode substrate.

2. The deformable mirror of claim 1, wherein the support plate has sufficient rigidity to suppress deformation of the electrode substrate caused by deformation stress of the electrode substrate to one-tenth or less of a distance between the electrodes.

3. The deformable mirror of claim 2, wherein the support plate has a reference surface for attachment.

4. The deformable mirror of claim 2, wherein a cable is connectable to the electrode substrate via a connector, and the support plate has sufficient rigidity to suppress deformation of the electrode substrate caused by deformation stress of the electrode substrate.

5. The deformable mirror of claim 2, wherein materials having generally the same expansion coefficients are selected as materials for the support plate and the electrode substrate.

6. The deformable mirror of claim 2, wherein the electrode substrate is made of a glass-epoxy resin material and the support plate is made of a stainless steel plate material.

7. A device for observing a retina of an eye using the deformable mirror according to claim 2.

8. The deformable mirror of claim 1, wherein the support plate has a reference surface for attachment.

9. The deformable mirror of claim 1, wherein a cable is connectable to the electrode substrate via a connector, and the support plate has sufficient rigidity to suppress deformation of the electrode substrate caused by deformation stress of the electrode substrate.

10. The deformable mirror of claim 1, wherein materials having generally the same expansion coefficients are selected as materials for the support plate and the electrode substrate.

11. The deformable mirror of claim 1, wherein the electrode substrate is made of a glass-epoxy resin material and the support plate is made of a stainless steel plate material.

12. A device for observing a retina of an eye using the deformable mirror according to claim 1.

13. A deformable mirror comprising:
    an electrode substrate having a plurality of electrodes formed on a surface of the electrode substrate;

a silicon membrane configured as a counter electrode, and having an electrode side opposed to the plurality of electrodes formed on the electrode substrate;

a reflection section provided on a side of the silicon membrane opposite the electrode side;

a spacer for maintaining a distance between the silicon membrane and the electrode substrate at a specific value; and a support plate integrally bonded to the electrode substrate for restraining deformation of the electrode substrate, wherein an area of the electrode substrate to which the support plate is integrally bonded includes an area of the silicon membrane, a spacer attaching area, and an electrode forming area in which the plurality of electrodes of the electrode substrate are formed.

14. A device for observing a retina of an eye using the deformable mirror according to claim 13.

* * * * *